(12) United States Patent
Wei et al.

(10) Patent No.: US 11,174,236 B2
(45) Date of Patent: Nov. 16, 2021

(54) METHOD FOR PREPARATION OF 1,4-SORBITAN

(71) Applicants: Lonza Guangzhou Pharmaceutical Ltd., Guangzhou (CN); Lonza Ltd, Visp (CH)

(72) Inventors: Jieping Wei, Guangzhou (CN); Yanling Yang, Guangzhou (CN); Daniel Shan, Guangzhou (CN); Reta Zhu, Guangzhou (CN); Paul Hanselmann, Brig-Glis (CH); Dieter Scherer, Laufen (CH)

(73) Assignees: Lonza Guangzhou Pharmaceutical Ltd., Guangzhou (CN); Lonza Ltd, Visp (CH)

(*) Notice: Subject to any disclaimer, the term of this patent is extended or adjusted under 35 U.S.C. 154(b) by 0 days.

(21) Appl. No.: 17/265,939

(22) PCT Filed: Aug. 26, 2019

(86) PCT No.: PCT/EP2019/072661
§ 371 (c)(1),
(2) Date: Feb. 4, 2021

(87) PCT Pub. No.: WO2020/043639
PCT Pub. Date: Mar. 5, 2020

(65) Prior Publication Data
US 2021/0261514 A1    Aug. 26, 2021

Related U.S. Application Data

(60) Provisional application No. 62/736,060, filed on Sep. 25, 2018.

(30) Foreign Application Priority Data

Aug. 27, 2018 (WO) ............... PCT/CN2018/102509
Sep. 25, 2018 (EP) ..................... 8196446
Jan. 14, 2019 (EP) ..................... 19151606
May 24, 2019 (EP) ..................... 19176534
Jun. 14, 2019 (EP) ..................... 19000293
Jul. 19, 2019 (EP) ..................... 19187318
Jul. 24, 2019 (EP) ..................... 19187974

(51) Int. Cl.
*C07D 307/20*    (2006.01)

(52) U.S. Cl.
CPC ............... *C07D 307/20* (2013.01)

(58) Field of Classification Search
CPC .................................. C07D 307/20
See application file for complete search history.

(56) References Cited

U.S. PATENT DOCUMENTS

| | | |
|---|---|---|
| 6,639,067 B1 | 10/2003 | Brinegar et al. |
| 2002/0002284 A1 | 1/2002 | Delgado et al. |
| 2016/0130277 A1 | 5/2016 | Gozlan et al. |

FOREIGN PATENT DOCUMENTS

| | | |
|---|---|---|
| CN | 106167476 | 11/2016 |

OTHER PUBLICATIONS

International Search Report and Written Opinion for PCT/EP2019/072661 dated Oct. 10, 2019.
Soltzberg et al., "Hexitol Anhydrides. Synthesis and Structure of Arlitan, the 1,4-Monoanhydride of Sorbitol," Journal of American Chemical Society, Jun. 18, 1946, No. 6, 3 pages.

*Primary Examiner* — Valerie Rodriguez-Garcia
(74) *Attorney, Agent, or Firm* — Dority & Manning, P.A.

(57) ABSTRACT

The invention discloses a method for preparation of 1,4-sorbitan by dehydration of D-sorbitol, wherein one equivalent of water is removed and a cyclization occurs, followed by a treatment with ethanol and isopropanol.

16 Claims, No Drawings

METHOD FOR PREPARATION OF 1,4-SORBITAN

CROSS REFERENCE TO RELATED APPLICATIONS

This application is the U.S. National Stage entry of International Application Number PCT/EP2019/072661 filed under the Patent Cooperation Treaty having a filing date of Aug. 26, 2019, which claims priority to U.S. Provisional Patent Application No. 62/736,060, having a filing date of Sep. 25, 2018, International Application Number PCT/CN2018/102509 filed under the Patent Cooperation Treating having a filing date of Aug. 27, 2018, European Patent Application No. 18196446.1 having a filing date of Sep. 25, 2018, European Patent Application No. 19151606.1 having a filing date of Jan. 14, 2019, European Patent Application No. 19176534.6 having a filing date of May 24, 2019, European Patent Application No. 19000293.1 having a filing date of Jun. 14, 2019, European Patent Application No. 19187318.1 having a filing date of Jul. 19, 2019, and European Patent Application No. 19187974.1 having a filing date of Jul. 24, 2019, which are incorporated herein by reference.

The invention discloses a method for preparation of 1,4-sorbitan by dehydration of D-sorbitol, wherein one equivalent of water is removed and a cyclization occurs, followed by a treatment with ethanol and isopropanol.

1,4-Sorbitan is used for the production of pharmaceuticals, such as certain prostaglandin analogues, and for the production of excipients used in formulation of pharmaceuticals, such as Polysorbate 80.

S. Stolzberg, J. Am. Chem. Soc., 1946, 68, 919-921, discloses a method for preparation of 1,4-sorbitan by a dehydration of 100 g sorbitol in the presence of concentrated sulfuric acid and water at ca. 140° C. for 30 min, the method has a recrystallization step from isopropanol as a last step, reported yield is 33 g; the calculated molar yield is 36.6%.

US 2002/0002284 A1 discloses a method for preparation of 1,4-sorbitan by dehydration of 4 kg D-sorbitol in the presence of sulfuric acid and water at 104° C. for ca. 52 h, the method has a recrystallization step from ethanol as a last step, reported yield is 1.693 kg, the calculated molar yield is 47.0%. Besides sulfuric acid, also $Na_2CO_3$, isopropanol, $Na_2SO_4$, ethanol, activated charcoal and toluene are used in considerable amounts. The method comprises 3 filtration steps besides the dehydration step and the recrystallization step.

CN 101948451 A discloses a method for preparation of high-purity 1,4-sorbitan, which is characterized by taking sorbitol as a raw material through two times of dehydration and three times of crystallization. Already after the second dehydration, a base is added to the reaction mixture for neutralization, then the reaction mixture is filtered to remove an acid catalyst used in the second dehydration reaction, the a decolourization is done by addition of activated carbon, which again necessitates a filtration for removing the activated carbon. The crystallization is done with methanol, after each crystallization step a filtration is done. The content of 1,4-sorbitan is 73.7% after the decolourization, 87% after the first, 94% after the second and 99.2% after the third crystallization. The yield after the decolourization was 70%, the yield after the three crystallization was 19%, so the overall yield was 13%.

CN 106167476 A discloses in [0028] S1 a preparation of 1,4-Sorbitan from a melt of sorbitol with a catalyst which is composed of tetrabutylammonium bromide and p-toluene sulfonic acid. No yield and also no analytical data is given of any amounts of sorbitol or of isosorbide in the product.

A reworking of this example as disclosed herein under "Comparative Example 1" showed inter alia, that the product is a sticky liquid, the yield is very low with 9.6% and there are still considerable amounts of D-sorbitol (ca. 28%) and of isosorbide (2.5%) in the product.

US 2016/0130277 A1 (US'277) discloses in Example 1 the dehydration of Sorbitol to provide 1,4-sorbitan. The reported yield of 35% is significantly lower than the yield of 52.6% of inventive Example 1.

Reworking of this Example 1 of US'277, as reported herein under Comparative Example 2, was not possible. In particular the crystallization of the reported residue after the reaction from cold methanol was not possible even though the procedure as reported in Example 1 US'277 up to this point was follow literally. The analysis of the this residue shows a significantly higher relative content of sorbitol and a significantly lower relative content of 1,4 sorbitan compared to the analysis of the equivalent intermediate in the clear solution in ethanol in the inventive example 1. This difference in the relative amounts of 1,4 sorbitan and sorbitol correlates well with the reported significantly lower yield of Example 1 of US'277. The reaction in Example 1 of US'277 is done under a pressure of 50 bar.

Any use of a compound for or in pharmaceutical applications requires a defined purity and usually also a high purity.

There was a need for a method for preparation 1,4-sorbitan with high yield, high purity, low content of isosorbide or D-sorbitol; the method should be as economic as possible, such as with a low number of steps such as filtration or with a low number of different chemicals used, also the method should be suited to be done "in one pot", meaning that only one reactor can be used.

Unexpectedly, a method was found which gives high yield, high purity, low content of isosorbide, low content D-sorbitol; the method is economic, has a low number of steps such as filtration and uses a low number of different chemicals. The method can be done in one reactor. The method provides 1,4-sorbitan with considerable higher yields and purity compared to the example [0028] S1 of CN 106167476 A.

Abbreviations

DMSO dimethyl sulfoxide equiv equivalent

Isosorbide compound of formula (3), MW 146.1 g/mol, CAS 652-67-5

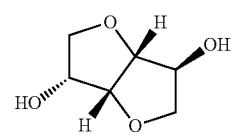

(3)

1,4-Sorbitan compound of formula (1), MW 164.2 g/mol, CAS 27299-12-3

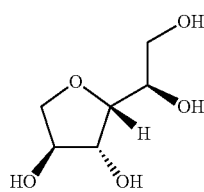

(1)

D-Sorbitol compound of formula (2), MW 182.2 g/mol, CAS 50-70-4

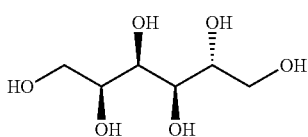

(2)

MW molecular weight
TBAB Tetrabutylammonium bromide
% percent are percent by weight (wt %), if not stated otherwise
Subject of the invention is a method for preparation of 1,4-sorbitan with four consecutive steps STEP1, STEP2, STEP3 and STEP4, wherein
in STEP1 D-sorbitol is dehydrated in a dehydration reaction DEHYDREAC in the presence of p-toluenesulfonic acid and tetrabutylammonium bromide, STEP1 provides a mixture MIX1;
in STEP2 ethanol is mixed with MIX1, STEP2 provides a mixture MIX2;
in STEP3 isopropanol is mixed with MIX2, STEP3 provides a mixture MIX3;
in STEP4 1,4-sorbitan is isolated from MIX3.
Preferably, the p-toluene sulfonic acid is used in form of p-toluenesulfonic acid monohydrate; so in any embodiment where p-toluene sulfonic acid is mentioned, the preferred embodiment is p-toluenesulfonic acid monohydrate.
Preferably, no solvent is present in or used for DEHYDREAC.
Preferably, no water is charged for DEHYDREAC.
Preferably, DEHYDREAC is done neat, that is only the three components D-sorbitol, p-toluenesulfonic acid and tetrabutylammonium bromide are used for and are charged for DEHYDREAC.
Preferably, the molar equivalent of p-toluenesulfonic acid in DEHYDREAC acid is from 0.2 to 1.6%, more preferably from 0.4 to 1.4%, even more preferably from 0.6 to 1.2%, especially from 0.6 to 1.0%, of the molar equivalents of D-sorbitol.
Preferably, the molar equivalent of tetrabutylammonium bromide in DEHYDREAC acid is from 1.0 to 3.6%, more preferably from 1.2 to 3.2%, even more preferably from 1.4 to 2.8%, especially from 1.6 to 2.4%, more especially from 1.6 to 2.0%, of the molar equivalents of D-sorbitol.
Preferably, the weight of ethanol mixed in STEP2 is from 0.2 to 5 fold, more preferably from 0.2 to 2 fold, even more preferably from 0.2 to 1 fold, especially from 0.2 to 0.8 fold, more preferably from 0.2 to 0.6 fold, even more especially from 0.3 to 0.5 fold, of the weight of D-sorbitol.

Preferably, the weight of isopropanol mixed in STEP2 is from 0.2 to 5 fold, more preferably from 0.2 to 2 fold, even more preferably from 0.2 to 1 fold, especially from 0.2 to 0.8 fold, more especially from 0.2 to 0.6 fold, even more especially from 0.3 to 0.5 fold, of the weight of D-sorbitol.
Preferably, DEHYDREAC is done at a temperature TEMP1, TEMP1 is from 95 to 130° C., more preferably from 95 to 120° C., even more preferably from 100 to 115° C., especially from 105 to 115° C., in particular 110° C.
Preferably, the reaction time TIME1-1 of DEHYDREAC is from 3 to 12 h, more preferably from 4 to 12 h, even more preferably from 5 to 10 h, especially from 5 to 8 h, more especially from 5 to 7 h, in particular 6 h.
In another embodiment, TIME1-1 is preferably from 6 to 10 h, more preferably from 7 to 9 h.
Preferably, DEHYDREAC is done at a pressure PRESS1 of 500 mbar or below, more preferably of 250 mbar or below, even more preferably of 100 mbar or below, especially of 50 mbar or below, more especially of 25 mbar or below, even more especially of 15 mbar or below, in particular of 10 mbar or below.
The lower limit of the pressure may be anything which is technically feasible. Examples for a lower limit of the pressure may be 0.1 mbar, or 0.5 mbar, or 1 mbar, or 2 mbar.
In another embodiment, DEHYDREAC is done at PRESS1 of from 0.001 to 500 mbar, preferably of from 0.001 to 250 mbar, more preferably of from 0.001 to 100 mbar, especially of from 0.001 to 50 mbar, more especially of from 0.01 to 25 mbar, even more especially of from 0.1 to 15 mbar, in particular of from 1 to 15 mbar, more in particular of from 1 to 12.5 mbar, even more in particular 4 to 6 mbar.
Preferably, STEP2, STEP3 and STEP4 are done at atmospheric pressure.
Water is formed by DEHYDREAC as the reaction is a dehydration, which removes 1 equiv of water. When the p-toluene sulfonic acid is used in form of p-toluenesulfonic acid monohydrate, it can also be a source of water during DEHYDREAC.
Preferably, water is removed during DEHYDREAC.
Preferably, STEP2 is done at a temperature TEMP2 of from 60 to 90° C., more preferably of from 60 to 85° C., even more preferably of from 65 to 80° C., in particular of from 70 to 75° C.
Preferably, STEP1 comprises a cooling COOL1 after DEHYDREAC, where MIX1 is cooled from TEMP1 to TEMP2.
Preferably, COOL1 is done in a time TIME1-2, TIME1-2 is from 10 min to 10 h, more preferably from 15 min to 5 h, even more preferably from 15 min to 2 h, especially from 20 min to 1 h, in particular in 30 min.
Preferably, is DEHYDREAC has been done at PRESS1, then the pressure can be brought back from PRESS1 to atmospheric pressure after DEHYDREAC. If STEP1 comprises COOL1 and DEHYDREAC has been done at PRESS1, then the pressure can be brought back from PRESS1 to atmospheric pressure before, during or after COOL1.
Preferably, after the mixing of ethanol, STEP2 comprises a stirring STIRR2 of MIX2 for a time TIME2-1, TIME2-1 is from 30 min to 10 h, more preferably of from 1 to 8 h, even more preferably of from 1 to 6 h, especially of from 1 to 4 h, more especially from 1.5 to 3 h, in particular 2 h.

Preferably, STIRR2 is done at TEMP2.

Preferably, STEP3 is done at a temperature TEMP3-1 of from 10 to 30° C., more preferably of from 15 to 25° C., even more preferably of from 17.5 to 22.5° C., in particular 20° C.

Preferably STEP2 comprises a cooling COOL2, where MIX2 is cooled from TEMP1 or TEMP2 to TEMP3-1.

Preferably, COOL2 is done after STIRR2.

Preferably, COOL2 is done from TEMP2 to TEMP3-1.

Preferably, STEP2 comprises STIRR2 and COOL2, and COOL2 is done after STIRR2.

Preferably, COOL2 is done in a time TIME2-2, TIME2-2 is from 1 to 10 h, more preferably from 1 to 8 h, even more preferably from 1 to 6 h, especially from 1 to 4 h, more especially from 2 to 4 h, in particular 3 h.

Preferably, after the mixing of isopropanol, STEP3 comprises a cooling COOL3 of MIX3 to a temperature TEMP3-2 of from −5 to 5° C., more preferably of from −2.5 to 2.5° C., even more preferably of from −1 to 2° C., in particular 0° C.

Preferably, COOL3 is done in a time TIME3-1, TIME3-1 is from 30 min to 10 h, more preferably of from 30 min to 8 h, even more preferably of from 30 min to 6 h, especially from 30 min to 4 h, more especially from 30 min to 2 h, in particular 1 h.

Preferably, STEP3 comprises a stirring STIRR3 of MIX3, STIRR3 is done for a time TIME3-2, TIME3-2 is from 1 to 12 h, more preferably from 1 to 10 h, even more preferably from 2 to 8 h, especially from 2 to 6 h, more especially from 3 to 5 h, in particular 4 h.

Preferably, STIRR3 is done after COOL3.

Preferably, STIRR3 is done at TEMP3-2.

More preferably, STIRR3 is done after COOL3 and STIRR3 is done at TEMP3-2.

The isolation in STEP4 of 1,4-sorbitan from MIX3 can be done by any means known to the skilled person, such as evaporation of any liquids in MIX3, filtration, centrifugation, drying, or a combination thereof, preferably the isolation is done by filtration or centrifugation of MIX3, more preferably by filtration, preferably followed by drying of the provided isolated solid product.

Preferably, 1,4-sorbitan is isolated in STEP4 from MIX3 by filtration providing a presscake, preferably followed by washing the presscake with isopropanol, preferably followed by drying of the washed presscake, preferably the drying is done at a temperature of from 30 to 70° C., more preferably of from 40 to 60° C., in particular 50° C.

In one embodiment,

STEP1 comprises consecutively DEHYDREAC and COOL1;

STEP2 comprises after the mixing of ethanol consecutively STIRR2 and COOL2;

STEP3 comprises after the mixing of isopropanol consecutively COOL3 and STIRR3;

STEP4 comprises an isolation of 1,4-sorbitan by a filtration of MIX3, preferably followed by washing and drying.

Preferably, in STEP2 ethanol is charged to MIX1 providing MIX2.

Preferably, in STEP3 isopropanol is charged to MIX2 providing MIX3.

Preferably, STEP1 and STEP2 are done consecutively without isolation, such as by filtration, of the 1,4-sorbitan between STEP1 and STEP2.

Preferably, STEP2 and STEP3 are done consecutively without isolation, such as by filtration, of the 1,4-sorbitan between STEP2 and STEP3.

More preferably, STEP1, STEP2 and STEP3 are done consecutively without isolation, such as by filtration, of the 1,4-sorbitan between STEP1 and STEP2 and without isolation, such as by filtration, of the 1,4-sorbitan between STEP2 and STEP3.

Preferably, STEP1, STEP2 and STEP3 are done consecutively in one and the same reactor.

There is no need to use camphorsulfonic acid, sulfuric acid, $Na_2CO_3$, $Na_2SO_4$, activated charcoal or toluene in the method of instant invention.

Preferably, no sulfuric acid is used in STEP1;

more preferably, no sulfuric acid is used in STEP1, STEP2, STEP3 or STEP4.

Preferably, no camphorsulfonic acid is used in STEP1;

more preferably, no camphorsulfonic acid is used in STEP1, STEP2, STEP3 or STEP4.

Preferably, no $Na_2CO_3$, $Na_2SO_4$, activated charcoal or toluene are used in STEP2 or STEP3; more preferably no $Na_2CO_3$, $Na_2SO_4$, activated charcoal or toluene are used in STEP2, STEP3 or STEP4;

even more preferably no $Na_2CO_3$, $Na_2SO_4$, activated charcoal or toluene are used in STEP1, STEP2, STEP3 or STEP4.

Preferably, the method of instant invention does not use azeotropic removal of water, more preferably azeotropic removal of water facilitated by the presence of toluene during the azeotropic removal of water for providing the azeotrope.

Preferably, after the isolation of the product in STEP4 there is no recrystallization, for example from EtOH.

More preferably, none of the steps STEP1, STEP2, STEP3 and STEP4 comprise a recrystallization after an isolation, for example from EtOH.

EXAMPLES

Materials

The materials were used in the following qualities, if not otherwise stated:

D-Sorbitol 98 wt %

TsOH—$H_2O$ 99 wt %

TBAB 98 wt %

Ethanol 99 wt %

Isopropanol 99 wt %

Methods:

(1) GC

Instrument Parameters

Column DB-1 HT (30 m*0.25 mm*0.1 m) Agilent Technologies, Santa Clara, USA

Temperature Program:

Initial; time 100° C.; 0 min

Rate1; Final 1; Time 1 8° C./min; 350° C.; keep 10 min

Run Time 41.25 min

Equilibration Time 0.5 min

Mode Cons. flow

Carrier gas $H_2$

Flow 1.5 ml/min

Split ratio 10:1

Inlet Temperature 350° C.

Injection Volumn 1 microliter

Detector temperature 350° C.

Sample Preparation

Sample Stock Solution

Add 2 g sample to 5 ml pyridine and 10 ml acetic anhydride in a screw-cap bottle (25 mL) and heat up to 120° C. for 2 hours under stirring.

Sample Solution 0.5 ml of Sample stock solution is added into an autosampler vial with 1 ml of dichloromethane and mixed 1,4-Sorbitan is detected at ca. 12.3 min.

(2) $^1$H NMR

Solvent: DMSO-d6

5 to 10 mg of sample were dissolved in 0.6 ml of DMSO-d6 and mixed.

(3) $^{13}$C NMR

Solvent: DMSO-d6

20 to 50 mg of sample were dissolved in 0.6 ml of DMSO-d6 and mixed well.

(4) Optical Rotation Method

Instrument Parameters

Instrument MCP 300 of Anton Paar GmbH, Graz, Austria

Wavelength 589 nm

Cell 100.00 mm

Temperature 20.0° C.

Response 2 s

Measure N=5

Delay 10 s

Stable Temperature ±0.3° C.

Sample Preparation

Blank

Pure water

Sample Solution

300±3 mg of 1,4-Sorbitan was added into a 100 ml volumetric flask, then dissolved with water and diluted to volume.

Example 1

D-sorbitol (300 g, 1.647 mol, 1 equiv) was charged into a 1.5 L reactor. p-Toluenesulfonic acid monohydrate (2.665 g, 0.014 mol, 0.0085 (0.85%) equiv) was charged, followed by charging of TBAB (9.6 g, 0.03 mol, 0.0182 (1.81%) equiv). Vacuum of reactor 4 to 6 mbar was applied. Then the mixture was heated to 110° C. (the mixture melted at around 90° C.) and stirred at 110° C. for 6 hours. The mixture was cooled to 70 to 75° C. in 30 min. Ethanol (150 mL) was charged. The resulting mixture was stirred at 70 to 75° C. for 2 hours and formed a clear solution. Then the solution was cooled to 20° C. in 3 hours. A yellow suspension was formed. Isopropanol (150 mL) was charged. The mixture was cooled to 0° C. in 1 hour. The mixture was slurry at 0° C. for 4 hours. The mixture was filtered, and the cake was washed with isopropanol (150 mL). The cake was dried at 50° C. for 16 hours under vacuum to provide 142.2 g of product as white solid.

Yield 52.6%

$^1$H NMR and $^{13}$C NMR confirmed the structure.

GC area-%:

1,4-Sorbitan 97%

Isosorbide 0.14%

D-Sorbitol 0.12%

Specific Rotation: −22.26°, c=3.1 (water)

Comparative Example 1

S1 of Example 1 of CN 106167476 A was repeated literally word by word. The translation of the example from Chinese into English was provided by a Chinese patent attorney:

S1 Adding solid sorbitol powder into the reactor; raising the temperature to 90° C.; stirring the powder in the reactor until it turns to a molten state; adding catalyst I, wherein the catalyst I is added in an amount of 4% by weight of the solid sorbitol powder, and the catalyst I is composed of tetrabutylammonium bromide and p-toluene sulfonic acid in a weight ratio of 3:2; and stirring the mixture uniformly; dehydrating the mixture for 2 hours at a temperature of 100° C. under the vacuum degree from 0.006 MPa; filtering, and treating the dehydrated mixture for 50 minutes by adding activated carbon when the temperature is lowered to 35° C., wherein the activated carbon is added in an amount of 0.3% of the total weight of the solid sorbitol powder and the catalyst I, and the activated carbon has an average particle diameter of 48 μm; and filtering, concentrating, and drying to obtain 1,4-Sorbitan.

The following results were obtained in this Comparative Example 1:

The product was a colorless and sticky liquid.

Yield: 9.6%

GC area-% of 1,4-Sorbitan: 56.9%

Isosorbide: 2.5%

D-Sorbitol: 28.7%

Observation:

From the beginning, that is from the melting of the solid sorbitol powder, until the end, that is the obtained product, the physical form is a sticky liquid. No solid product is obtained in any stage of the process.

Comparative Example 2

Example 1 of US 2016/0130277 A1 in [0048] was repeated literally in the following way:

D-Sorbitol (20 g, 110 mmol) and 0.10% (mol mol) camphorsulfonic acid are added in a 150 ml stainless steel autoclave. The reactor is sealed hermetically, purged with hydrogen three times and then hydrogen was introduced up to a pressure of 50 bar. The system is then heated to 140° C. and shaken with a mechanical shaker for 15 hours. After cooling to room temperature, the hydrogen pressure was released and the white foam was diluted in ethanol (200 ml) in order to obtain a yellow homogeneous mixture. Solvent is evaporated under reduced pressure.

According to the description of this Example 1 the obtained residue should now be crystallized from cold methanol followed by vacuum filtration.

This crystallization was tried several times with different amounts of methanol and with different temperatures but surprisingly it was not possible to do such crystallization. Even when cooling the solution in methanol to 0° C. no crystallization occurred.

GC analysis revealed a GC area-% of:

1,4 sorbitan 54.90% sorbitol 32.420%

This residue of Example 1 of US'277 can be compared with the product obtained in Example 1 of this invention at the following point in the procedure of Example 1 of this invention:

After having stirred at 110° C. for 6 hours, the mixture was cooled to 70 to 75° C. in 30 min. Ethanol (150 mL) was charged. The resulting mixture was stirred at 70 to 75° C. for 2 hours and formed a clear solution.

GC analysis of this clear solution in EtOH revealed a GC area-% of:

1,4 sorbitan 74.97% sorbitol 2.870%

It is assume that the much higher content of sorbitol in the residue that was obtained in this reworking of Example 1 of US'277 in Comparative Example 2 prevented crystallization. of said residue No reason for the non-working of the crystallization can be found in the way how the reworking was carried out, the procedure given in Example 1 of US'277 was followed literally until said residue.

In any case the relative content of the desired 1,4 sorbitan is significantly lower and the relative content of undesired sorbitol is significantly higher in this residue of Example 1 of US'277 when compared with the equivalent reaction mixture in form of the clear solution in EtOH of the inventive Example 1.

This difference in the relative amounts of these two substances correlates with the significantly lower yield of 35% reported in Example 1 of US'277, compared to the yield of 52.6% of inventive Example 1.

This difference in the yields shows that the process of the invention is an improved procedure compared with the process of Example 1 of US'277.

The invention claimed is:

1. A method for preparation of 1,4-sorbitan with four consecutive steps STEP1, STEP2, STEP3 and STEP4, wherein
   in STEP1 D-sorbitol is dehydrated in a dehydration reaction DEHYDREAC in the presence of p-toluenesulfonic acid and tetrabutylammonium bromide,
   the reaction time TIME1-1 of DEHYDREAC is from 3 to 12 h;
   DEHYDREAC is done at a temperature TEMP1, TEMP1 is from 95 to 130° C.,
   DEHYDREAC is done at a pressure PRESS1 of 500 mbar or below,
   STEP1 provides a mixture MIX1;
   in STEP2 ethanol is mixed with MIX1, STEP2 provides a mixture MIX2;
   in STEP3 isopropanol is mixed with MIX2, STEP3 provides a mixture MIX3;
   in STEP4 1,4-sorbitan is isolated from MIX3.
2. The method according to claim 1, wherein the p-toluene sulfonic acid is used in form of p-toluenesulfonic acid monohydrate.
3. The method according to claim 1, wherein DEHYDREAC is done neat, wherein only the three components D-sorbitol, p-toluenesulfonic acid and tetrabutylammonium bromide are used for and are charged for DEHYDREAC.
4. The method according to claim 1, wherein DEHYDREAC is done at a temperature TEMP1, TEMP1 is from 95 to 120° C.
5. The method according to claim 1, wherein the reaction time TIME1-1 of DEHYDREAC is from 4 to 12 h.
6. The method according to claim 1, wherein DEHYDREAC is done at a pressure PRESS1 of 250 mbar or below.
7. The method according to claim 1, wherein water is removed during DEHYDREAC.
8. The method according to claim 1, wherein STEP2 is done at a temperature TEMP2 of from 60 to 90° C.
9. The method according to claim 1, wherein STEP3 is done at a temperature TEMP3-1 of from 10 to 30° C.
10. The method according to claim 1, wherein after the mixing of isopropanol, STEP3 comprises a cooling COOL3 of MIX3 to a temperature TEMP3-2 of from −5 to 5° C.
11. The method according to claim 1, wherein STEP3 comprises a stirring STIRR3 of MIX3, wherein STIRR3 is done for a time TIME3-2, wherein TIME3-2 is from 1 to 12 h.
12. The method according to claim 11, wherein STIRR3 is done after COOL3, wherein COOL3 comprises a cooling of MIX3 to a temperature TEMP3-2 of from −5 to 5° C.
13. The method according to claim 11, wherein STIRR3 is done at TEMP3-2, wherein TEMP3-2 is a temperature of from −5 to 5° C.
14. The method according to claim 1, wherein 1,4-sorbitan is isolated in STEP4 from MIX3 by filtration.
15. The method according to claim 1, wherein STEP1, STEP2 and STEP3 are done consecutively in one and the same reactor.
16. A method for preparing prostaglandin analogues or Polysorbate comprising preparing 1,4-sorbitan according to claim 1.

* * * * *